(12) United States Patent
Reah et al.

(10) Patent No.: US 12,115,082 B2
(45) Date of Patent: Oct. 15, 2024

(54) INTER VERTEBRAL DEVICES

(71) Applicant: AXIS SPINE TECHNOLOGIES LTD, St. Albans (GB)

(72) Inventors: Christopher Reah, St. Albans (GB); Jonathan Arcos, St. Albans (GB); Nicholas Sandham, London (GB)

(73) Assignee: AXIS SPINE TECHNOLOGIES LTD, Hertfordshire (GB)

( * ) Notice: Subject to any disclaimer, the term of this patent is extended or adjusted under 35 U.S.C. 154(b) by 705 days.

(21) Appl. No.: 17/294,681

(22) PCT Filed: Nov. 19, 2019

(86) PCT No.: PCT/GB2019/053273
§ 371 (c)(1),
(2) Date: May 17, 2021

(87) PCT Pub. No.: WO2020/104788
PCT Pub. Date: May 28, 2020

(65) Prior Publication Data
US 2022/0015919 A1    Jan. 20, 2022

(30) Foreign Application Priority Data
Nov. 19, 2018   (GB) .................................... 1818847

(51) Int. Cl.
*A61F 2/44*     (2006.01)
*A61F 2/30*     (2006.01)

(52) U.S. Cl.
CPC .... *A61F 2/447* (2013.01); *A61F 2002/30266* (2013.01); *A61F 2002/30331* (2013.01);
(Continued)

(58) Field of Classification Search
CPC .............................. A61F 2/4455–2/447; A61F 2250/0004–2250/001; A61F 2250/0048;
(Continued)

(56) References Cited

U.S. PATENT DOCUMENTS

| 6,045,579 A | 4/2000 | Hochshuler et al. |
| 6,102,950 A | 8/2000 | Vaccaro |

(Continued)

FOREIGN PATENT DOCUMENTS

| EP | 2719360 | 4/2014 |
| WO | 2013184946 | 12/2013 |
| WO | 2014093136 | 6/2014 |

OTHER PUBLICATIONS

Product Brochure "Aero-LL Lateral Lumbar Interbody and Fixation System", Stryker Spine, 2016, pp. 1-52.
(Continued)

*Primary Examiner* — Eduardo C Robert
*Assistant Examiner* — Angel Roberto Mora-Velazquez
(74) *Attorney, Agent, or Firm* — LIU & LIU

(57) ABSTRACT

The present invention relates to an intervertebral fusion device (10) comprising a superior component (20), an inferior component (40), and a core component (80) inserted there between. The intervertebral fusion device further comprises first and second retention mechanisms which resist ejection of the core component from between the superior and inferior components. Each of the first and second retention mechanisms comprises first and second portions. One of the first and second portions is unitary with one of the superior and inferior components. The other of the first and second portions is unitary with the core component. The first and second portions each comprise an inter-engaging formation which are urged in an opposite direction. The first inter-engaging formation is urged to inter-engage with the
(Continued)

second inter-engaging formation upon insertion of the core component between the superior and inferior components.

21 Claims, 4 Drawing Sheets

(52) U.S. Cl.
    CPC .............. *A61F 2002/30383* (2013.01); *A61F 2002/30505* (2013.01); *A61F 2002/3054* (2013.01)

(58) Field of Classification Search
    CPC .. A61F 2002/30537; A61F 2002/30398; A61F 2002/304; A61F 2002/30401; A61F 2002/30375; A61F 2002/30359; A61F 2002/30383
    See application file for complete search history.

(56) References Cited

U.S. PATENT DOCUMENTS

| | | | |
|---|---|---|---|
| 6,113,637 | A | 9/2000 | Gill et al. |
| 8,308,804 | B2 | 11/2012 | Krueger |
| 8,388,686 | B2 | 3/2013 | Aebi et al. |
| 9,402,739 | B2 | 8/2016 | Weiman et al. |
| 9,526,628 | B2 | 12/2016 | Krueger |
| 9,585,765 | B2 | 3/2017 | Niemiec et al. |
| 9,801,734 | B1 | 10/2017 | Stein et al. |
| 2002/0143399 | A1 | 10/2002 | Sutcliffe |
| 2004/0254644 | A1 | 12/2004 | Taylor |
| 2006/0015183 | A1 | 1/2006 | Gilbert et al. |
| 2007/0270957 | A1* | 11/2007 | Heinz .................. A61F 2/4465 623/17.11 |
| 2007/0276498 | A1 | 11/2007 | Aebi et al. |
| 2008/0294260 | A1* | 11/2008 | Gray .................. A61B 17/8047 623/17.15 |
| 2011/0153020 | A1 | 6/2011 | Abdelgany et al. |
| 2011/0184522 | A1 | 7/2011 | Melkent et al. |
| 2013/0006357 | A1* | 1/2013 | Krueger .................. A61F 2/44 623/17.13 |
| 2013/0085573 | A1* | 4/2013 | Lemoine ............... A61F 2/4465 623/17.16 |
| 2013/0103153 | A1 | 4/2013 | Blackwell et al. |
| 2013/0158667 | A1 | 6/2013 | Tabor et al. |
| 2015/0164494 | A1 | 6/2015 | Glazer |
| 2015/0320568 | A1 | 11/2015 | Ameil et al. |
| 2016/0116396 | A1 | 4/2016 | Hunt et al. |
| 2016/0166396 | A1 | 6/2016 | McClintock |
| 2016/0213483 | A1 | 7/2016 | To et al. |
| 2017/0239063 | A1 | 8/2017 | Predick |
| 2018/0000606 | A1 | 1/2018 | Hessler et al. |
| 2018/0036141 | A1 | 2/2018 | O'Neil et al. |
| 2018/0098860 | A1 | 4/2018 | To et al. |
| 2018/0256357 | A1 | 9/2018 | To et al. |

OTHER PUBLICATIONS

International Search Report of Counterpart PCT International Application No. PCT/GB2019/053273.
International Search Report of Counterpart PCT International Application No. PCT/GB2019/053275.
International Search Report of Counterpart PCT International Application No. PCT/GB2019/053277.

* cited by examiner

INTER VERTEBRAL DEVICES

FIELD OF THE INVENTION

The present invention relates to intervertebral devices and more specifically to intervertebral fusion devices.

BACKGROUND TO THE INVENTION

Adjacent vertebrae in the spinal column are coupled to each other by an intervertebral disc. The intervertebral disc holds the adjacent vertebrae together and functions as a cushion between the vertebrae whilst allowing for relative movement of the vertebrae. Problems with intervertebral discs arise from one or more of a range of diseases and conditions. A surgical procedure, such as spinal fusion, may be used to address such problems. A typical spinal fusion procedure involves partial or full removal of a problematic intervertebral disc and installation of an intervertebral device in the place of the partially or fully removed intervertebral disc.

Known intervertebral devices are of varied form and function. Many known intervertebral devices are configured to provide for adjustment of height and functional spine unit angle to address differing extents of removal of an intervertebral disc, differing anatomy and spinal deformity. Furthermore, ease of assembly, installation, including reduced impaction loads during insertion, and disassembly are design objects for known intervertebral devices aside from issues of manufacturability and cost. Some known intervertebral devices are characterised by their complexity with such complexity being liable to result in compromise on ease of assembly, installation and disassembly, in compromise on long-term reliability, or in risk to the patient, such as from wear of material from the intervertebral device over time and loss of spinal correction.

The present inventors have become appreciative of shortcomings of known intervertebral devices, such as the shortcomings mentioned above. The present invention has been devised in light of the inventors' appreciation of such shortcomings. It is therefore an object for the present invention to provide an improved intervertebral device and more specifically an improved intervertebral fusion device. It is a further object for the present invention to provide an improved method of installing an intervertebral device in an intervertebral space between first and second adjacent vertebrae and more specifically an improved method of installing an intervertebral fusion device.

STATEMENT OF INVENTION

According to a first aspect of the present invention there is provided an intervertebral fusion device comprising:
 a superior component having a superior component top side and a superior component bottom side, the superior component being configured to be received in an intervertebral space between first and second vertebrae whereby the superior component top side abuts against the first vertebra;
 an inferior component having an inferior component top side and an inferior component bottom side, the inferior component being configured to be received in the intervertebral space between the first and second vertebrae whereby the inferior component bottom side abuts against the second vertebra, the superior component bottom side and the inferior component top side opposing each other when the superior and inferior components are received in the intervertebral space;
 a core component configured for insertion between the superior and inferior components whereby a separation between the superior and inferior components is determined; and
 first and second retention mechanisms operative to resist ejection of the core component from between the superior and inferior components,
 wherein each of the first and second retention mechanisms comprises a first portion and a second portion, one of the first and second portions being unitary with one of the superior and inferior components and the other of the first and second portions being unitary with the core component,
 wherein the first portion comprises a first inter-engaging formation which is urged in an inter-engaging direction orthogonal to each of a direction of insertion of the core component between the superior and inferior components and a direction of separation of the superior and inferior components, the inter-engaging direction of the first retention mechanism being opposite the inter-engaging direction of the second retention mechanism, and
 wherein the second portion comprises a second inter-engaging formation, the first inter-engaging formation being urged to inter-engage with the second inter-engaging formation upon insertion of the core component between the superior and inferior components.

The intervertebral fusion device comprises three main components, namely a superior component, an inferior component and a core component. In use, the superior and inferior components are placed in an intervertebral space between first and second vertebrae formed by at least partial removal of a problematic intervertebral disc. The superior component has a superior component top side and a superior component bottom side with the superior component being placed in the intervertebral space such that the superior component top side faces the first vertebra or what might remain of a partially removed intervertebral disc. The inferior component has an inferior component top side and an inferior component bottom side with the inferior component being placed in the intervertebral space such that the inferior component bottom side faces the second vertebra or what might remain of a partially removed intervertebral disc. The superior component bottom side and the inferior component top side oppose each other when the superior and inferior components are received in the intervertebral space. The superior and inferior components may be in registration with each other when in the intervertebral space and more specifically when the core component is fully inserted between the superior and inferior components as described below.

The core component is configured for insertion between the superior and inferior components. In use, the core component may be inserted between the superior and inferior components when the superior and inferior components have been placed in the intervertebral space, as described above. Upon insertion the core component determines a separation between the superior and inferior components and hence a height of the intervertebral fusion device with the superior component top side abutting against the first vertebra or what remains of the partially removed intervertebral disc and with the inferior component bottom side abutting against the second vertebra or what remains of the partially removed intervertebral disc. Differing heights of intervertebral fusion device may be provided by selection from plural core components of different height.

As mentioned above, an intervertebral disc functions as a shock absorber. An intervertebral disc is therefore under load with the pattern of loading varying and repeating over an extended period. When installed in place of the intervertebral disc, the intervertebral fusion device is likewise under load with such loading being liable to eject the core component from between the superior and inferior components. Usually, such loading provides for ejection to an inconsiderable extent at any one time. Nevertheless, such fractional ejection can become appreciable over time. Ejection is a risk for a core component of any shape, such as a core component having substantially parallel upper and lower surfaces, and not just a risk for the wedge-shaped core component described below. The intervertebral fusion device therefore further comprises first and second retention mechanisms. The first and second retention mechanisms are operative to resist ejection of the core component from between the superior and inferior components.

Each of the first and second retention mechanisms comprises a first portion and a second portion. One of the first and second portions is unitary with one of the superior and inferior components. The superior or inferior component may be formed by the like of casting, moulding or printing whereby one of the first and second portions is integrally formed with the superior or inferior component. Alternatively, the superior or inferior component may be formed by the like of machining or stamping and one of the first and second portions may be formed separately from the superior or inferior component by the like of machining or stamping. The thus formed separate portion may then be attached to the thus formed superior or inferior component by welding, a press fit mechanism or the like whereby the portion is unitary with the superior or inferior component.

In a form, the first portion may be unitary with one of the superior and inferior components. Having the first portion on the superior component or the inferior component in preference to the core component may minimise the amount of material used in the core component and thereby afford an aperture of greater extent in the core component for admitting bone graft material to the interior of the spinal fusion device.

Loading of the intervertebral fusion device is usually from above the superior component. If the superior and inferior components are both gripped by their adjacent vertebrae, loading from above will tend to eject the core component from between the superior and inferior components. However, if the core component and the inferior component are held firmly together, such loading is more liable to push the superior component down onto the core component than eject the core component. Therefore, in a more specific form of the intervertebral fusion device, the first portion may be unitary with the inferior component.

The first portion comprises a first inter-engaging formation. Furthermore, the first portion is configured to urge the first inter-engaging formation in an inter-engaging direction orthogonal to each of a direction of insertion of the core component between the superior and inferior components and a direction of separation of the superior and inferior components. Each of the first and second retention mechanisms therefore has its respective inter-engaging direction of movement of first inter-engaging formation. More specifically, the inter-engaging direction of the first retention mechanism is opposite the inter-engaging direction of the second retention mechanism. Such a structure involving first and second retention mechanisms working in opposite directions may hold the core component sufficiently to provide adequate resistance to ejection of the core component.

The first and second retention mechanisms may be spaced apart from each other and more specifically may be spaced apart from each other in a direction transverse to a direction of insertion of the core component between the superior and inferior components. More specifically, the first and second retention mechanisms may be spaced apart from each other in a direction orthogonal to each of a direction of insertion of the core component between the superior and inferior components and a direction of separation of the superior and inferior components. The first and second retention mechanisms may be on opposite sides of the core component upon insertion of the core component between the inferior and superior components. Holding the core component at its opposite sides may provide a firm hold on the core component.

The second portion comprises a second inter-engaging formation. The second inter-engaging formation may be immovable in relation to the component, such as the core component, in which it is comprised. The second inter-engaging formation may therefore be a profile, such as a recess, defined on a surface of the component in which the second inter-engaging formation is comprised. As mentioned above, the first portion is configured to urge the first inter-engaging formation in the inter-engaging direction. When so urged and upon insertion of the core component between the superior and inferior components, the first inter-engaging formation inter-engages with the second inter-engaging formation. Inter-engagement of the first and second inter-engaging formations of each of the first and second retention mechanisms provides for resistance to ejection of the core component from between the superior and inferior components when the intervertebral fusion device is subject to load and perhaps also when the intervertebral fusion device is subject to load over time.

The intervertebral fusion device may further comprise third and fourth retention mechanisms. Each of the third and fourth retention mechanisms may have a form as described above in respect of the first and second retention mechanisms. The first and second retention mechanisms may be constituted in the core component and the inferior component. The third and fourth retention mechanisms may be constituted in the core component and the superior component. The intervertebral fusion device may thus be configured to provide for resistance to movement of the core component relative to the inferior component and the superior component. It is advantageous to provide for resistance to movement of the core component relative to both the inferior component and the superior component.

Each of the first and second inter-engaging formations may be at a location on a respective one of the inferior or superior component and the core component whereby the first inter-engaging formation inter-engages with the second inter-engaging formation upon insertion of the core component between the inferior and superior components to a predetermined extent at which the first and second inter-engaging formations are in registration with each other. More specifically, the first and second inter-engaging formations may be at locations whereby there is inter-engagement of the first and second inter-engaging formations when the core component is fully inserted between the inferior and superior components.

The core component may have an upper side and a lower side. When the core component is inserted between the inferior and superior components, the upper side may face the superior component bottom side and the lower side may face the inferior component top side. The core component may have first and second lateral sides which each face in a direction orthogonal to a direction of insertion of the core component and to a direction of separation of the inferior and superior components, with the first and second lateral sides facing in opposite directions. An inter-engaging formation, such as a recess, may be located on each of the first and second lateral sides.

The upper side and a lower side of the core component may be inclined to each other. The core component may therefore have the form of a wedge. Furthermore, the upper side and a lower side may not meet at an acute angle whereby the core component has the form of a frustum of a wedge. The core component and the inferior and superior components may be configured for insertion of the thinner edge of the thinner and thicker edges of the core component. An inclination of the inferior and superior components relative to each other may thus be determined by way of the core component further to a separation between the inferior and superior components. Extent of inclination of the inferior and superior components may be determined by selection from a plurality of core components having upper and lower sides of different inclinations. Such selection may be combined with selection from a plurality of core components having different heights. Where the intervertebral fusion device comprises a core component in the form of a wedge, loading of the intervertebral fusion device is more liable to eject the core component from between the inferior and superior components. It may therefore be desirable for the intervertebral fusion device to comprise first to fourth retention mechanisms, as described above, rather than a subset thereof to provide for proper retention of the core component between the inferior and superior components.

The first portion may be configured to urge the first inter-engaging formation in the inter-engaging direction by way of a spring bias. The first portion may therefore further comprise a sprung portion which urges the first inter-engaging formation in the inter-engaging direction. The sprung portion may be a cantilever spring. The sprung portion may be straight or tapered. Tapering controls stiffness and hence extent of deflection. A cantilever sprung structure may be simpler and more compact than other means of providing spring bias. A more compact structure is desirable in an intervertebral fusion device in which space is usually at a premium. As described below, the cantilever sprung structure may lie along a direction of insertion of the core component between the superior and inferior components whereby little space is occupied by the cantilever sprung structure in the transverse direction.

The first inter-engaging formation may be spaced apart on the cantilever spring from a proximal end of the cantilever spring. The first inter-engaging formation may comprise a protrusion. The second inter-engaging formation may comprise a recess with the recess and protrusion being configured for reception of the protrusion in the recess to thereby provide for inter-engagement. The first portion may have the form of a finger having the first inter-engaging formation towards a distal end of the finger. The first portion may extend in a direction of insertion of the core component between the inferior and superior components. A proximal end of the first portion may be located towards an edge of an inferior or superior component that first receives the core component when the core component is inserted. Having the proximal end located towards the core component receiving edge means that the first portion may be less liable to damage when the core component is inserted between the inferior and superior components. As mentioned above, the first portion is unitary with one of the inferior or super components and the core component and, more specifically, may be unitary with one of the inferior or super components in a form of the intervertebral fusion device. The component with which the first portion is unitary may be formed of a material, such as one of the materials described below, of sufficient yield strength to provide the spring bias.

As mentioned above, the first inter-engaging formation may comprise a protrusion and the second inter-engaging formation may comprise a recess with the recess and protrusion being configured for reception of the protrusion in the recess to thereby provide for inter-engagement. Reception of the protrusion in the recess may be perceived by the surgeon, such as by way of an audible click or a reduction in force as the core component advances, whereby the surgeon is notified that the intervertebral fusion device is properly assembled. Furthermore, this structure may allow for trial insertion of a core component or several different core components in turn but without full insertion to the extent of inter-engagement to assess degree of spinal alignment, for example before committing to full insertion of a selected core component. Assessment of such trial insertion may be assisted by a known imaging technique.

At least one of the protrusion and the recess may have a sloping side whereby the protrusion rides down the sloping side as extent of insertion of the core component increases. Furthermore, configuration of the first portion to urge the protrusion in the inter-engaging direction by way of the spring bias may draw the core component between the superior and inferior components under the force of the spring bias. The core component may thus be fully inserted between the superior and inferior components.

Where the first inter-engaging formation is comprised in one of the superior and inferior components, the first inter-engaging formation may be at a first distance from an edge of the inferior or superior component that first receives the core component when the core component is inserted. Furthermore, and where the second inter-engaging formation is comprised in the core component, the second inter-engaging formation may be at a second distance from an edge of the core component opposite an edge that is first received between the superior and inferior components, the first distance being greater than the second distance. Such a structure may provide for the core component being pulled fully between the superior and inferior components by way of the spring bias described above. Furthermore, and where the core component and the inferior or superior component comprise respective inter-engaging anterior formations, the inter-engaging anterior formations may be brought into inter-engagement by the spring bias and by virtue of the first distance being greater than the second distance.

The inter-engaging anterior formations may be configured to draw the superior or inferior component and the core component together. The inter-engaging anterior formations may therefore comprise cooperating surface profiles that cooperate to move the superior or inferior component and the core component together as an extent of insertion of the core component between the superior and inferior components increases. At least one of the inter-engaging anterior formation on the core component and the inter-engaging anterior formation on the superior or inferior component may be sloped with a direction of the slope being such that the superior or inferior component and the core component are drawn together. The spring bias exerted by the first inter-engaging formation may therefore provide force to draw the core component between the superior and inferior components and also to draw the superior or inferior component and the core component together. In a form of the device, the inter-engaging anterior formation may be on the superior component whereby the superior component is drawn down onto the core component.

The device may comprise a further pair of inter-engaging anterior formations. A first one in the further pair of inter-engaging anterior formations may be comprised in the inferior component and a second one in the further pair may be comprised in the core component. The further pair of inter-engaging anterior formations may be configured to resist ejection of the core component from between the superior and inferior components. The first inter-engaging anterior formation may have the form of a recess and the second inter-engaging anterior formation may comprise a protrusion which is received in the recess to present resistance to ejection. The second inter-engaging anterior formation may further comprise a cantilever spring on which the protrusion is defined, the cantilever spring urging the protrusion in a direction of separation of the superior and inferior components whereby the protrusion is urged into the recess of the first inter-engaging anterior formation.

The core component and the respective one of the inferior and superior components may be configured in respect of their relative dimensions to move the first inter-engaging formation against its spring bias at the end of a first stage of insertion of the core component between the inferior and superior components. More specifically, and where the first inter-engaging formation is comprised in one of the superior and inferior components, a leading edge of the core component may be bevelled whereby the first inter-engaging formation is progressively deflected against the spring bias as the first inter-engaging formation rides up the bevelled edge. Energy may thus be stored in the first portion to provide for urging of the first inter-engaging formation towards inter-engagement. The first and second inter-engaging formations may be brought into inter-engagement by way of the spring bias during a second stage of insertion following the first stage of insertion.

As described above, the first portion may extend in a direction of insertion of the core component between the inferior and superior components. The first portions of the first and second retention mechanisms may extend in substantially parallel directions. Where the first portions are comprised in the inferior or superior component, the first portions may be located towards lateral sides of the inferior or superior component.

The core component and at least one of the inferior component and superior component may comprise respective inter-engaging posterior formations. Where an inter-engaging posterior formation is comprised in the superior component, the inter-engaging posterior formation of the superior component and the inter-engaging posterior formation of the core component may be configured to draw the superior component and the core component together. The inter-engaging posterior formations may therefore comprise cooperating surface profiles, with, for example, at least one surface profile being sloped, that cooperate to move the superior component and the core component together as an extent of insertion of the core component between the superior and inferior components increases. The spring bias exerted by the first inter-engaging formation, which is described above, may provide force to cause cooperation between the surface profiles and draw the superior component and the core component together. In addition, a distal edge of an inter-engaging posterior formation, and more specifically the distal edge of the inter-engaging posterior formation on the core component, may be configured to deflect when cooperating with the other inter-engaging posterior formation with inherent spring bias of the material of the deflecting inter-engaging posterior formation exerting force to draw the superior component and the core component together.

The superior component, the inferior component and the core component may be separate components. Having separate inferior and superior components and core component means that the components may be introduced to the intervertebral space more gently compared with known single piece intervertebral fusion devices which often need to be hammered into place. Such a less gentle insertion process may damage the intervertebral fusion device, may increase time required for the intervertebral fusion device to settle in the intervertebral space, and may result in trauma to vertebral bodies, adjacent soft tissues including neural structures. On the subject of trauma, a device that is hammered into place is liable to create microfractures in the vertebrae which could lead to subsidence of the device into the host bone. Furthermore, having separate components and in particular a core component separate to the inferior and superior components allows for differences in dimensions of intervertebral spaces, differences in angle between the adjacent vertebrae that define the intervertebral space, and degree of spinal alignment and/or correction. Each of the superior component, the inferior component and the core component may be integrally formed. The superior component and the inferior component may not engage with each other, other than by way of the core component.

Each of the inferior and superior components may have the form of a plate, albeit a plate having structures thereon that provide for mechanical engagement with the core component, whereby it is thin relative to its length and width. At least one of the superior component top side and the inferior component bottom side may be shaped in the coronal or sagittal planes, for example domed, to enhance fit and contact with the adjacent vertebrae.

References herein to anterior or to anterior aspect are to the anterior aspect of the intervertebral fusion device itself and not to the anterior aspect of the patient. The anterior aspect of the intervertebral fusion device itself therefore means the aspect at which the core component is inserted between the superior and inferior components. Correspondingly, references herein to posterior or to posterior aspect are to the posterior aspect of the intervertebral fusion device itself and not to the posterior aspect of the patient. The anterior and posterior aspects are oppositely directed. The intervertebral fusion device may be an anterior, anterior oblique, lateral or direct lateral intervertebral fusion device.

At least one of the superior component top side and the inferior component bottom side may be configured to provide for fusion. For example, the top or bottom side may comprise formations, such as protrusions, which, in use, engage with the bone of the vertebra. By way of another example, the top and/or bottom side may define apertures for passage of bone graft material therethrough from an interior of the intervertebral fusion device. By way of a further example, the top or bottom side may have a coating thereon or impregnation therein. The coating or impregnation may comprise material that provides for bone adhesion and/or bone formation to encourage bone to grow up to and bond onto the intervertebral fusion device to thereby provide long term stable attachment. One or more known coatings may be used, such as porous mesh, tricalcium phosphate (TCP), hydroxyapatite (HA) or bone morphogenetic protein (BMP).

At least one of the superior component, the core component and the inferior component may be formed from a metal, such as titanium, or a metal alloy, such as stainless steel, Ti6Al4V, CoCr or nitinol. Nitinol may be useful in respect of cooperating parts of the superior component, the core component and the inferior component. At least one of the superior component, the core component and the inferior component may be formed from a plastics material and more specifically a thermoplastic polymer, such as PEEK or carbon reinforced PEEK. In forms of the invention, the core component may be formed by 3D printing whereby the core component has the form of a 3D lattice. The aforementioned materials may be used to form the core component by way of 3D printing.

When assembled, the intervertebral fusion device may have a range of length by width from 20 mm by 15 mm to 65 mm by 50 mm. Where there is an oblique intervertebral fusion device, the range of length by width may be from 20 mm by 15 mm to 40 mm by 35 mm. Where there is an anterior intervertebral fusion device, the range of length by width may be from 20 mm by 20 mm to 50 mm by 50 mm. Where there is a lateral intervertebral fusion device, the range of length by width may be from 40 mm by 18 mm to 65 mm by 40 mm. A height of the intervertebral fusion device may be 5 mm to 15 mm at the posterior aspect.

According to a second aspect of the present invention there is provided a method of installing an intervertebral fusion device in an intervertebral space between first and second adjacent vertebrae, the intervertebral fusion device comprising a superior component having a superior component top side and a superior component bottom side, an inferior component having an inferior component top side and an inferior component bottom side, and a core component, the method comprising:

positioning the superior component and the inferior component relative to each other such that the superior component bottom side and the inferior component top side oppose each other;

inserting the core component between the superior and inferior components whereby a separation between the superior and inferior components is determined; and disposing the intervertebral fusion device in the intervertebral space such that the superior component top side abuts against the first vertebra and the inferior component bottom side abuts against the second vertebra, wherein the intervertebral fusion device comprises first and second retention mechanisms operative to resist ejection of the core component from between the superior and inferior components, each of the first and second retention mechanisms comprising a first portion and a second portion, one of the first and second portions being unitary with one of the superior and inferior components and the other of the first and second portions being unitary with the core component, wherein the first portion comprises a first inter-engaging formation which is urged in an inter-engaging direction orthogonal to each of a direction of insertion of the core component between the superior and inferior components and a direction of separation of the superior and inferior components, the inter-engaging direction of the first retention mechanism being opposite the inter-engaging direction of the second retention mechanism, and wherein the second portion comprises a second inter-engaging formation, the first inter-engaging formation being urged to inter-engage with the second inter-engaging formation upon insertion of the core component between the superior and inferior components.

The intervertebral fusion device may be installed in an intervertebral space by positioning the superior component and the inferior component relative to each other in the intervertebral space before the core component is inserted between the superior and inferior components. Alternatively, the intervertebral fusion device may be installed in an intervertebral space by positioning the superior component and the inferior component relative to each other at a location apart from the intervertebral space and inserting the core component between the superior and inferior components at this location before the thus assembled intervertebral fusion device is installed in the intervertebral space.

Further embodiments of the second aspect of the present invention may comprise one or more features of the first aspect of the present invention.

BRIEF DESCRIPTION OF DRAWINGS

The present invention will now be described by way of example only with reference to the following drawings, of which.

DESCRIPTION OF EMBODIMENTS

Figure 1A:
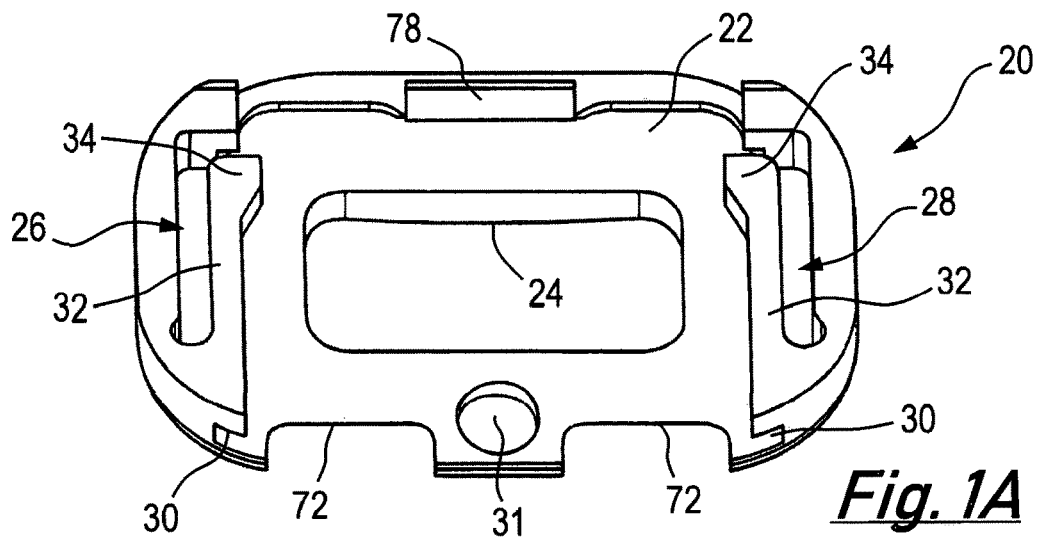
FIG. 1A shows a superior component of a first embodiment of the present invention.
Figure 1B:
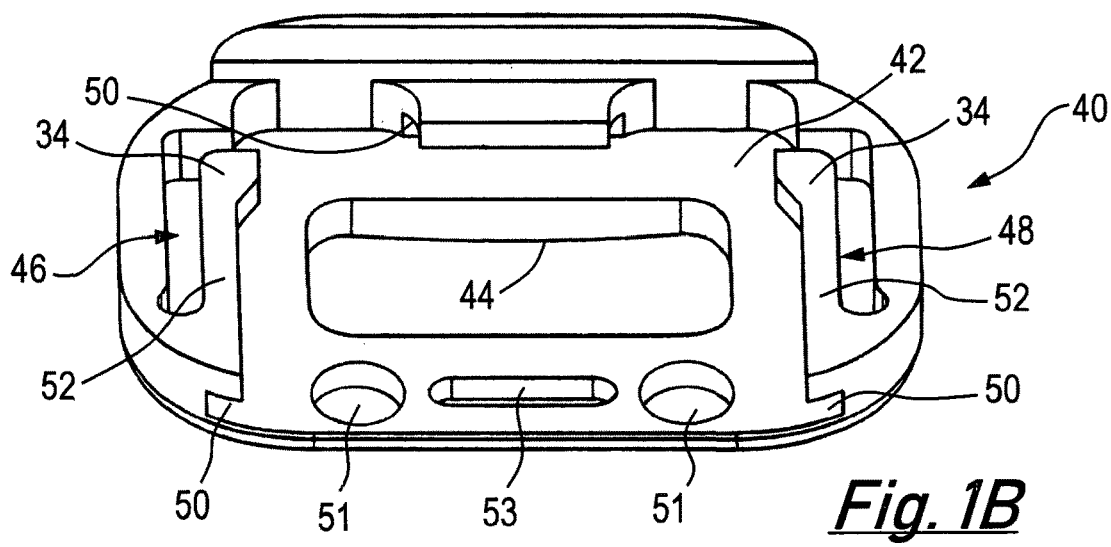
FIG. 1B shows an inferior component of the first embodiment of the present invention.
Figure 1C:
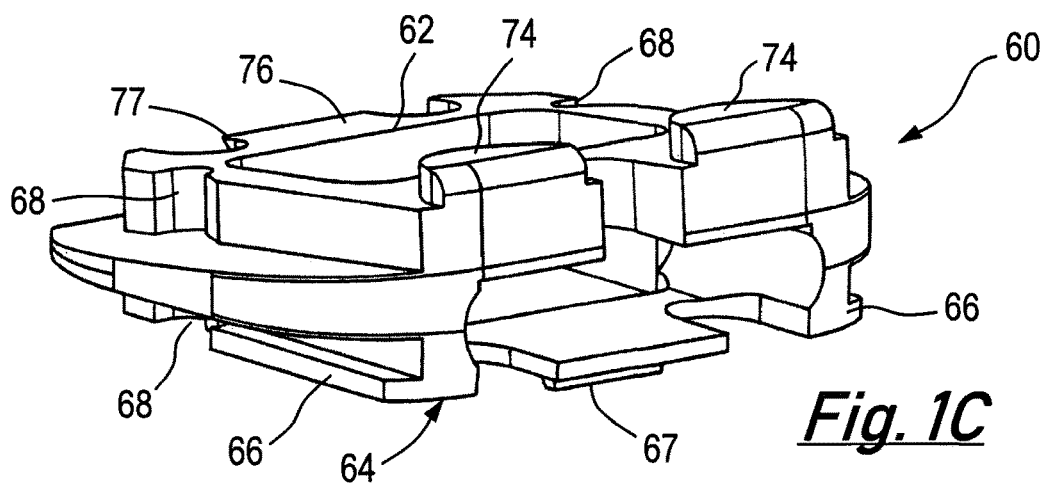
FIG. 1C shows core component of the first embodiment of the present invention.
Figure 2A:
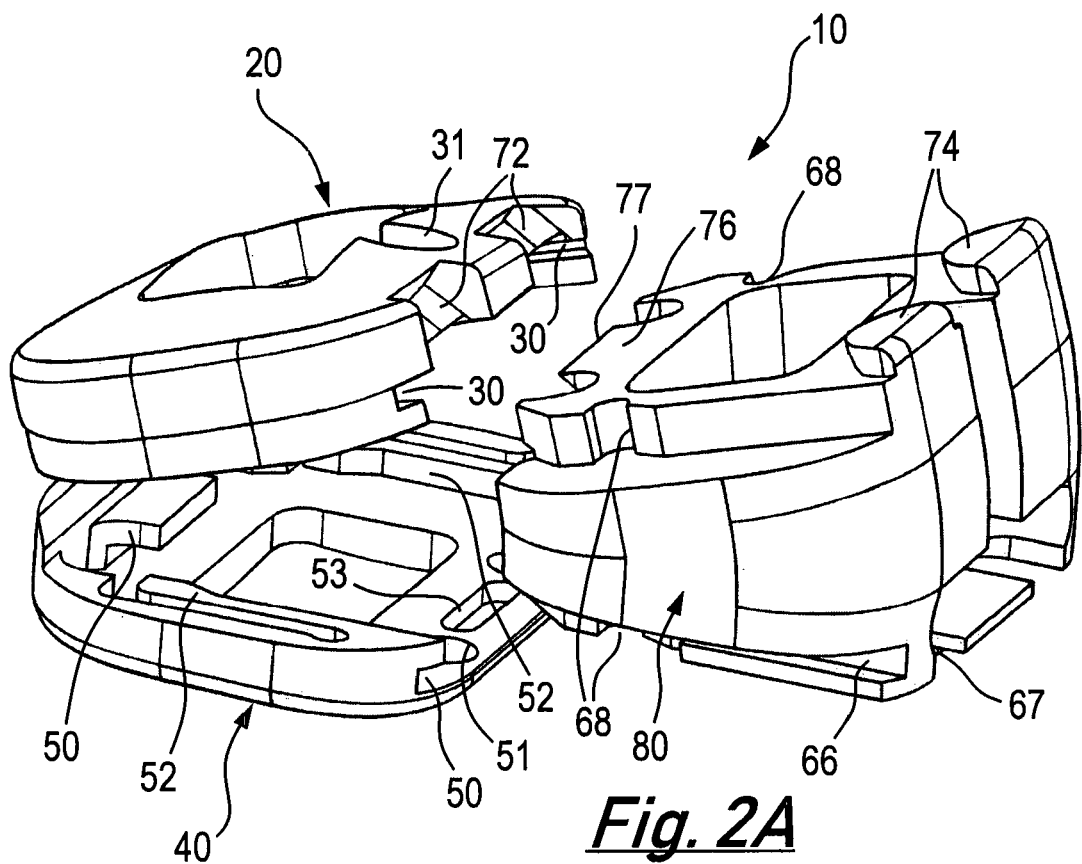
FIG. 2A shows the core component before insertion between the superior and inferior components according to a second embodiment.
Figure 2B:
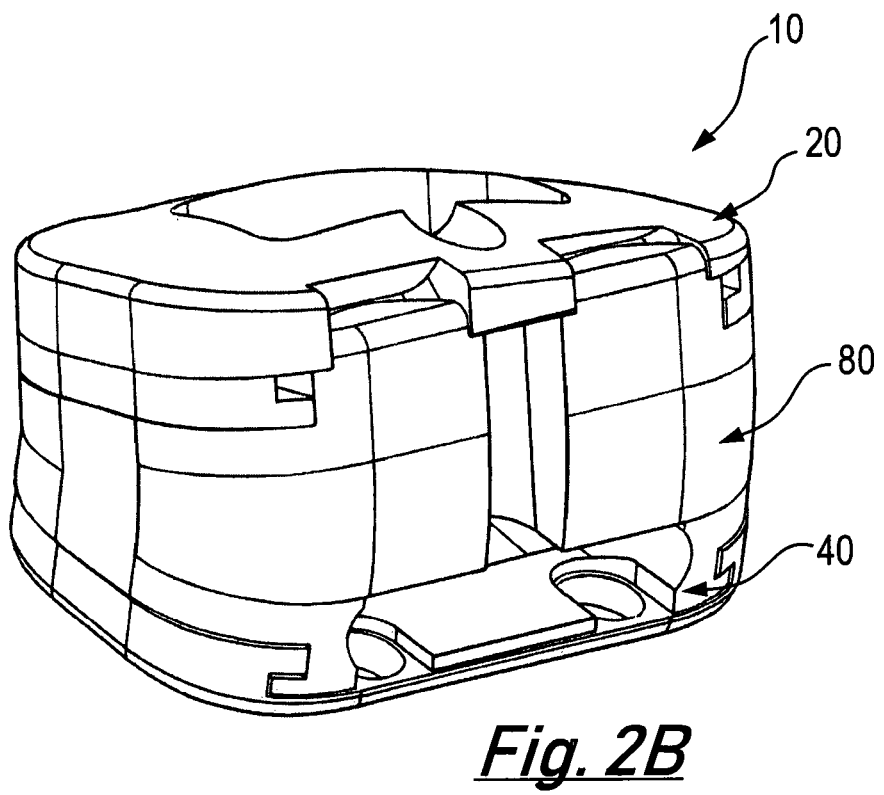
FIG. 2B shows the core component after insertion between the superior and inferior components according to the second embodiment.
Figure 3A:
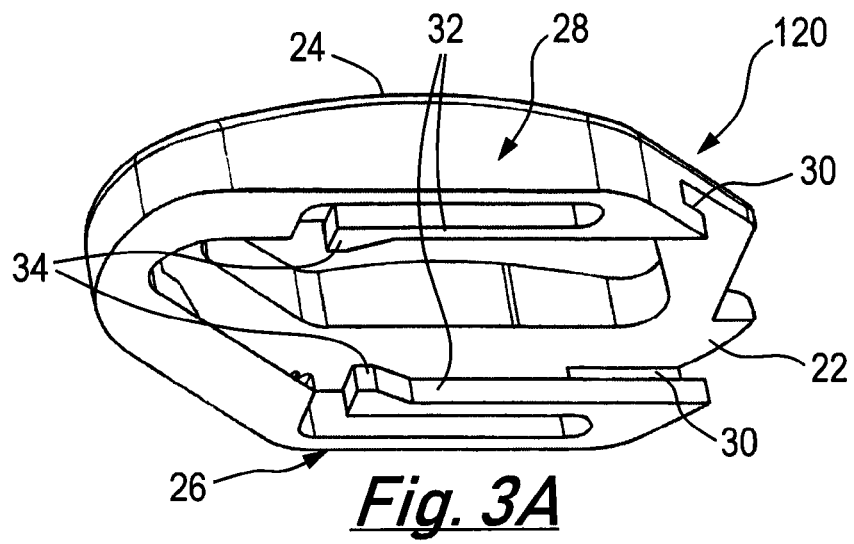
FIG. 3A shows a superior component of a third embodiment of the present invention.
Figure 3B:
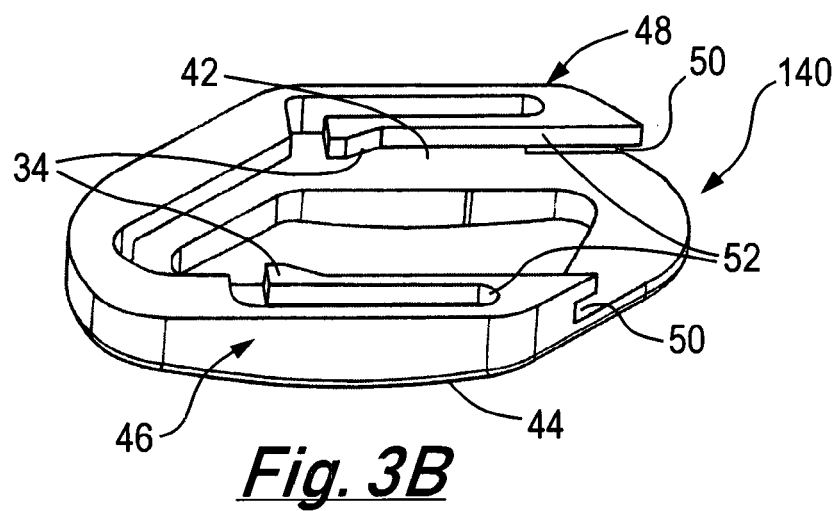
FIG. 3B shows an inferior component of the third embodiment of the present invention.
Figure 3C:
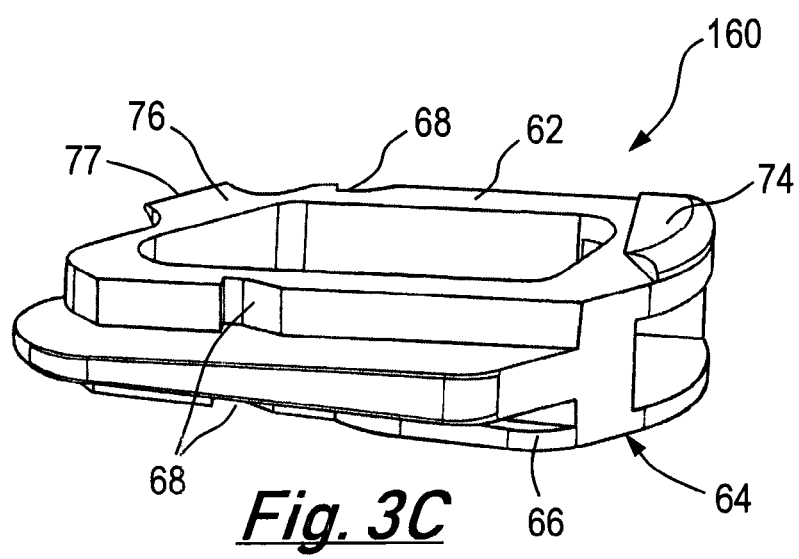
FIG. 3C shows core component of the third embodiment of the present invention.

A superior component, an inferior component and a core component of a first embodiment of intervertebral fusion device 10 are shown respectively in FIGS. 1A, 1B and 1C. The intervertebral fusion device 10 is an anterior lumbar interbody fusion (ALIF) device. FIG. 2A shows a core component before insertion between the superior and inferior components of FIGS. 1A and 1B according to a second embodiment of intervertebral fusion device with the second embodiment differing from the first embodiment in respect of the greater height of the core component of the second embodiment. FIG. 2B shows the core component of FIG. 2A after insertion between the superior and inferior components.

As mentioned above, the intervertebral fusion device 10 of FIGS. 1A to 2B comprises a superior component 20, an inferior component 40 and a core component 60, 80. Each of the superior component 20 and the inferior component 40 is generally of the form of a plate, albeit a plate having structures thereon and a large aperture through the centre thereof. The core component 60, 80 has the form of a frustum of a wedge. As can be seen from comparison of FIG. 1C with FIGS. 2A and 2B, the core component of FIG. 1C is thinner than the core component of FIGS. 2A and 2B. What is shown in FIGS. 2A and 2B therefore constitutes a second embodiment. Use of core components of different thicknesses and/or different extents of tapering wedge and with the same superior component 20 and inferior component 40 provides for different heights and angles of intervertebral fusion device 10. When the intervertebral fusion device 10 is being brought into use, the superior component 20 and the inferior component 40 are placed in the intervertebral space. It should be noted that the superior component 20 is shown in FIG. 1A upside down so that the features of the underside of the superior component can be seen. In use, the superior component 20 of FIG. 1A is turned upside down when inserted into the intervertebral space. The core component 60, 80 is positioned relative to the superior component 20 and the inferior component 40 as shown in FIG. 2A. Then the core component 60, 80 is positioned between edges of the superior component 20 and the inferior component 40 with the thin edge of the wedge shape of the core component foremost before the core component is progressively inserted between the superior component and the inferior component until fully received between the superior component and the inferior component. FIG. 2B shows the intervertebral fusion device 10 when the core component 60, 80 is fully received between the superior component 20 and the inferior component 40. When in the disposition shown in FIG. 2B, the superior component top side abuts against a first vertebra defining the intervertebral space in part and the inferior component bottom side abuts against a second vertebra defining the intervertebral space in part.

According to an alternative approach to use of the intervertebral fusion device 10, the intervertebral fusion device 10 is assembled outside the intervertebral space, as described above, before the assembled intervertebral fusion device is inserted into the intervertebral space.

The superior component 20 will now be described further with reference to FIG. 1A. The superior component 20 has a superior component bottom side 22, a superior component top side 24, a first lateral side 26 and a second lateral side 28. The superior component 20 comprises various formations 30, 31, 72, 78 on the superior component bottom side 22 which inter-engage with formations on the core component and provide for guided alignment and engagement between core component and superior component during progressive insertion of the core component. The formations 30, 31, 72, 78 also provide for secure attachment of core component and superior component to each other when the core component is fully received in the superior component. The superior component 20 defines a circular aperture 31 towards its anterior edge. The circular aperture 31 allows for reception therethrough of a screw which is driven into the adjacent vertebra. The superior component 20 further comprises two first portions 32 which are integrally formed with the superior component. One of the first portions 32 is located towards the first lateral side 26 and the other of the first portions 32 is located towards the second lateral side 28. Each of the first portions 32 comprises a main body in the form of a finger which extends from a proximal end of the finger at an anterior edge of the superior component across the superior component towards the posterior edge of the superior component. The first portion 32 therefore extends in a direction of insertion of the core component. The first portion 32 is unsupported and attached along its length with the exception of its proximal end. The superior component and hence the first portion 32 are formed of a material of sufficient yield strength that the first portion functions as a cantilever spring. Although not shown in FIG. 1A, the finger is tapered in certain forms to determine stiffness and hence extent of deflection. Furthermore, a radius of the interface between the finger and the part of the superior component from which the finger extents is determined to control stiffness of the finger. The main body of the first portion 32 defines a protrusion 34 (which constitutes a first inter-engaging formation) at its distal end with the protrusion 34 extending in a transverse direction of the superior component. The two first portions 32 are mirror images of each other whereby their two protrusions 34 oppose each other and extend towards each other. In view of the cantilever sprung nature of each first portion 32, application of a load to the protrusion 34 in a transverse direction towards a respective lateral side deflects the main body to thus store energy in the first portion to provide for urging of the protrusion 34 in the opposite direction. As described below, the main body of the finger is deflected by a leading edge of the core component bearing against the protrusion 34.

The inferior component 40 will now be described further with reference to FIG. 1B. The inferior component 40 has an inferior component top side 42, an inferior component bottom side 44, a first lateral side 46 and a second lateral side 48. Like the superior component 20, the inferior component 40 comprises various formations 50 on the inferior component top side 42 which inter-engage with formations on the core component and provide for engagement between core component and inferior component during progressive insertion of the core component. The formations 50 also provide for secure attachment of core component and inferior component to each other when the core component is fully received in the inferior component. However, the form and disposition of the formation 50 at the posterior of the inferior component 40 differs from the form and disposition of the formation 78 at the posterior of the superior component 20. The inferior component 40 defines two circular apertures 51 towards its anterior edge which are spaced apart from each other in the transverse direction. Each circular aperture 51 allows for reception therethrough of a screw which is driven into the adjacent vertebra. The inferior component 40 further comprises two first portions 52 which are integrally formed with the inferior component. One of the first portions 52 is located towards the first lateral side 46 and the other of the first portions 52 is located towards the second lateral side 48. The first portion 52 at the first lateral side 46 of the inferior component is of the same form and function as the first portion 32 at the first lateral side 26 of the superior component. The first portion 52 at the second lateral side 48 of the inferior component is of the same form and function as the first portion 32 at the second lateral side 28 of the superior component. The reader's attention is therefore directed to the preceding description of the two first portions 32 of the superior component 20.

The core component 60 will now be described further with reference to FIG. 1C. As described above, the core component 60 has the form of a frustum of a wedge. The core component 60 has an upper side 62 and a lower side 64, the core component 60 being configured to be inserted between the superior and inferior components 20, 40 such that the upper side 62 faces the superior component bottom side 22 and the lower side 64 faces the inferior component top side 42. This orientation of core component 60 in relation to superior and inferior components 20, 40 is obtained by various formations 66, 67, 74, 76 on the upper and lower sides 62, 64 with the formations on the upper side being of different form and disposition to the formations on the lower side. Furthermore, the formations 66, 67, 74, 76 on each side of the core component correspond to and provide for engagement with a respective one of the formations 30, 31, 72, 78 on the superior component and the formations 50 on the inferior component. The core component 60 defines four recesses 68 having sloping sides (each recess constitutes a second inter-engaging formation). Two of the recesses are located towards the upper side and two of the recesses are located towards the lower side. Furthermore, the recesses are located towards the thin edge of the wedge. Each of the recesses 68 faces in a transverse direction away from the core component.

As described above, the superior and inferior components 20, 40 are placed in the intervertebral space and the core component 60, 80 is positioned relative to the superior and inferior components as shown in FIG. 2A before the core component is inserted between the superior and inferior components. As the leading edge of the core component 60, 80 reaches the protrusions 34 of the superior and inferior components 20, 40 during insertion, the leading edge of the core component bears against each of the protrusions causing deflection of each of the four first portions 32, 52. The part of the leading edge that bears against a respective protrusion is bevelled to provide for increasing deflection as the extent of insertion of the core component is increased. Upon further insertion the protrusions 34 and the recesses 68 come into registration and each of the protrusions is urged under spring bias into a corresponding one of the recesses. Reception of the protrusions in their respective recesses produces an audible click which indicates to the surgeon that the core component is fully inserted. Inter-engagement between protrusions 34 and recesses 68 contributes to holding the core component 60, 80, and superior and inferior components 20, 40 together and more importantly presents resistance to ejection of the core component from between the superior and inferior components during use of the intervertebral fusion device 10.

As mentioned above, each of the recesses 68 on the core component 60 has sloping sides. When the core component is inserted to the extent that a protrusion 34 reaches its respective recess, the spring bias of the finger causes the protrusion to ride down the sloped side of the recess and thereby exert force to draw the core component further between the superior and inferior components. Further to this, the protrusion 34 is at a first distance from an anterior edge of the inferior or superior component and the recess 68 is at a second distance from an anterior edge of the core component with the first distance being slightly greater than the second distance. These relative distances in combination with the spring bias pull the core component fully between the superior and inferior components.

The core component 60 has two anterior formations 74 on its upper side 62 in the form of protrusions which are spaced apart from each other in the transverse direction along the anterior edge of the core component. Each anterior formation 74 has a side oriented towards the posterior edge of the core component which slopes away from a distal surface of the anterior formation towards the anterior edge. The superior component 20 has two recesses 72 which are spaced apart from each other in the transverse direction and which are defined in the anterior edge of the superior component. When the core component is nearly fully inserted between the inferior and superior components, a base of each recess 72 bears against the sloping side of its respective anterior formation 74 with further insertion causing the base to ride along the sloping side. As the base rides along the sloping side, the superior component is drawn down onto the core component. The pulling of the core component fully between the superior and inferior components by the spring bias, as described above, also causes the base to ride along the sloping side whereby the spring bias also draws the superior component down at its anterior edge onto the core component. The first distance being slightly greater than the second distance, as described above, causes the superior component to be drawn closely against the core component.

The core component 60 has a posterior formation 76 in the form of a protrusion which extends from the posterior edge of the core component adjacent the upper side 62 of the core component. An upper surface of the posterior formation 76 is defined by the upper side 62 of the core component. A distal edge of the posterior formation 76 slopes downwards from a distal edge 77 at the upper surface of the posterior formation and towards the posterior edge of the core component to define a slope. The superior component 20 has a posterior formation 78 in the form of a protrusion which extends from the posterior edge of the superior component in a direction opposite the direction of insertion of the core component over the superior component bottom side 22. The posterior formation 78 defines a distal surface which faces towards the inferior component when the inferior and superior components are aligned. A side of the posterior formation 78 oriented towards the anterior edge of the superior component slopes from an edge of the distal surface furthest from the posterior edge upwards and towards the posterior edge. When the core component is nearly fully inserted between the inferior and superior components, the slope defined by the posterior formation 76 of the core component and the slope defined by the posterior formation 78 of the superior component ride over each other to draw the superior component down onto the core component. The pulling of the core component fully between the superior and inferior components by the spring bias, as described above, also causes the slopes defined by the two posterior formations 76, 78 to ride over each other whereby the spring bias also draws the superior component down at its posterior edge onto the core component. The distal edge 77 at the upper surface of the posterior formation 76 of the core component is configured by virtue of the thinness of the distal edge having regard to the material properties of the core component to deflect when cooperating with the posterior formation 78 of the superior component. Inherent spring bias of the material of the posterior formation 76 adjacent the distal edge 77 exerts force to draw the superior component and the core component together to thereby provide a further means of drawing the superior component down at its posterior edge onto the core component.

Referring to FIG. 1C, the core component 60 further comprises in its lower side 64 a living hinge which defines a protrusion 67 thereon. Inherent spring bias of the living hinge urges the protrusion 67 towards the inferior component 40 when the core component 60 is received between the superior and inferior components 20, 40. When the core component 60 is at full insertion, the protrusion 67 on the living hinge at the lower side 64 of the core component is urged by the inherent spring bias of the living hinge into an elongate aperture 53 in the inferior component near the anterior edge of the inferior component. Reception of the protrusion 67 in the elongate aperture 53 presents a barrier to ejection of the core component from between the inferior and superior components.

Figure 4A:
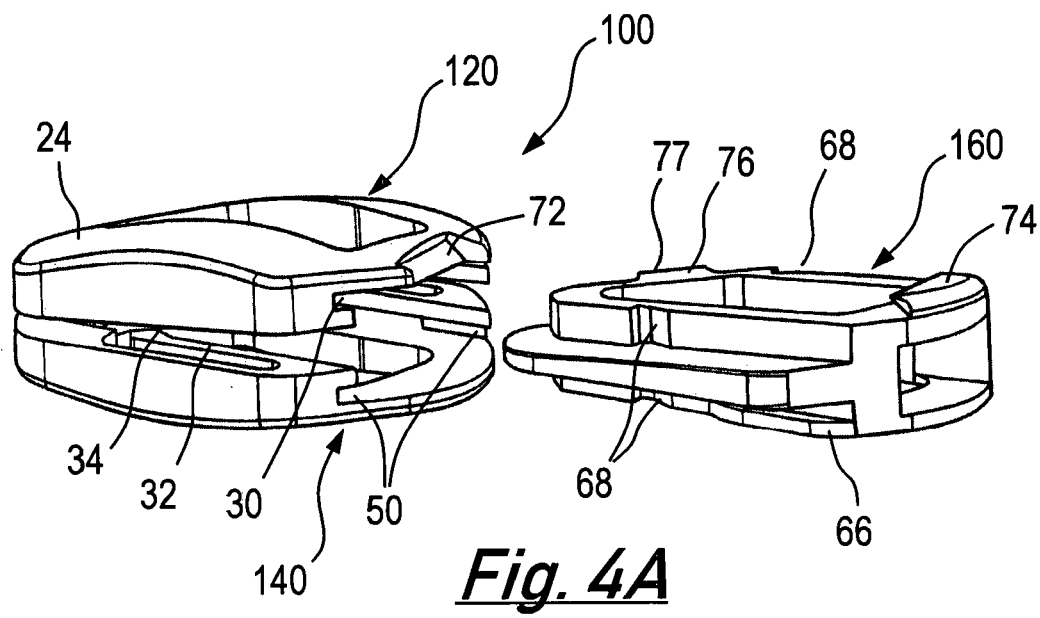
FIG. 4A shows the core component before insertion between the superior and inferior components according to the third embodiment.
Figure 4B:
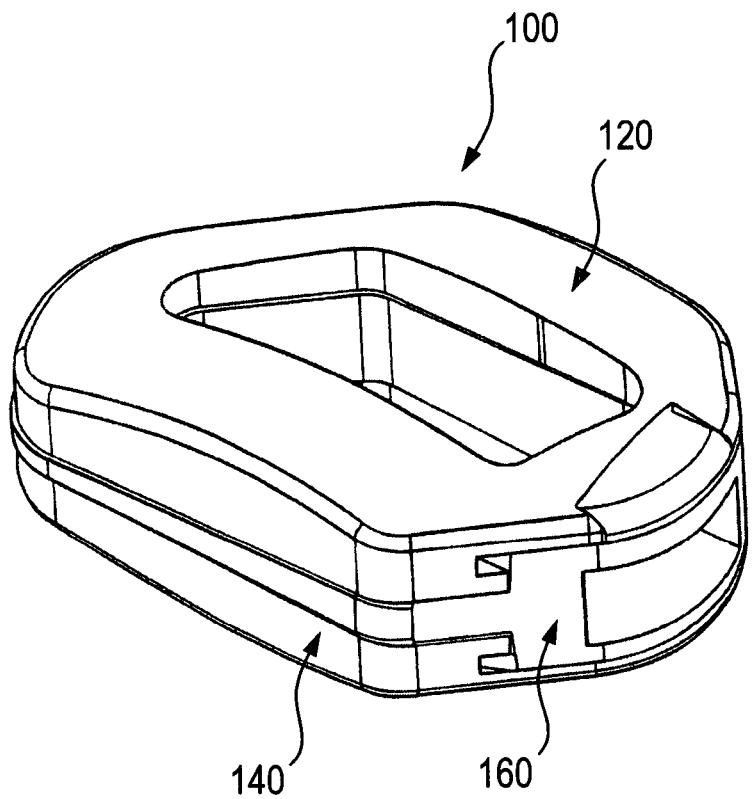
FIG. 4B shows the core component after insertion between the superior and inferior components according to the third embodiment.

A third embodiment of intervertebral fusion device 100 is shown in FIGS. 3A to 4B. The intervertebral fusion device 100 according to the third embodiment is an oblique lateral interbody fusion device. A superior component 120, an inferior component 140, and a core component 160 of the third embodiment are shown respectively in FIGS. 3A, 3B and 3C. FIG. 4A shows the core component 160 of the third embodiment before insertion between the superior and inferior components 120, 140 of FIGS. 3A and 3B. FIG. 4B shows the core component 160 of the third embodiment after insertion between the superior and inferior components 120, 140 of FIGS. 3A and 3B. The superior component 120, the inferior component 140, and the core component 160 of the third embodiment are of different shape and dimensions to the first and second embodiments when viewed in plan whereby the third embodiment is configured for insertion into an intervertebral space from an oblique lateral direction. Otherwise, and except as described below, the third embodiment is configured in respect of key features in the same fashion as the first and second embodiments. Such key features are therefore indicated in FIGS. 3A to 4B by the same reference numerals as for the first and second embodiments and the reader's attention is directed to the preceding description for a description of such key features. In respect of differences, as can be seen from FIG. 3C, the core component 160 has one anterior formation 74 on its upper side instead of the two anterior formations 74 of the first and second embodiments. Correspondingly, the superior component 120 of the third embodiment has one recess 72 at its anterior edge instead of the two recesses of the first and second embodiments. Furthermore, the third embodiment lacks the first and second embodiments' combination of the protrusion 67 on the living hinge in the core component and the elongate aperture 53 in the inferior component.

The invention claimed is:

1. An intervertebral fusion device, comprising:
a superior component having a superior component top side and a superior component bottom side, the superior component configured to be received in an intervertebral space between first and second vertebrae whereby the superior component top side abuts against the first vertebra;
an inferior component having an inferior component top side and an inferior component bottom side, the inferior component configured to be received in the intervertebral space between the first and second vertebrae whereby the inferior component bottom side abuts against the second vertebra, the superior component bottom side and the inferior component top side opposing each other when the superior and inferior components are received in the intervertebral space;
a core component configured for insertion between the superior and inferior components whereby a separation between the superior and inferior components is determined, the core component having first and second lateral sides which each face in a transverse direction which is orthogonal to a direction of insertion of the core component and to a direction of separation of the inferior and superior components, the first and second lateral sides facing in opposite directions;
a first retention mechanism comprising a first finger and a first recess; and
a second retention mechanism comprising a second finger and a second recess,
wherein a proximal end of each of the first and second fingers is attached to the superior or inferior component at an anterior end of the inferior or superior component that first receives the core component when the core component is inserted between the superior and inferior components whereby the finger is unitary with the superior or inferior component, and the finger is unsupported and unattached along its length except at its proximal end whereby the finger flexes along its length relative to the inferior or superior component,
wherein the proximal end of the first finger is attached at a first lateral side of the inferior or superior component and the first finger extends in the direction of insertion towards a posterior end of the inferior or superior component, and the proximal end of the second finger is attached at a second lateral side of the inferior or superior component and the second finger extends in the direction of insertion towards the posterior end of the inferior or superior component whereby the first and second fingers are spaced apart from each other in the transverse direction,
wherein the first finger defines a first protrusion at a distal end thereof and the second finger defines a second protrusion at a distal end thereof, the first and second protrusions spaced apart from and facing each other in the transverse direction,
wherein the first and second recesses are defined respectively on the first and second lateral sides of the core component and near a posterior end of the core component, and
wherein the first and second lateral sides of the core component are received between the first and second fingers during a first stage of insertion of the core component from first reception of the core component between the superior and inferior components to thereby guide the core component, the posterior end of the core component bearing against the first and second protrusions at the end of the first stage of insertion to flex the first and second fingers apart in the transverse direction, and during a second stage of insertion following the first stage of insertion the first and second protrusions are received in the first and second recesses respectively under spring bias exerted by the first and second fingers to thereby present resistance to ejection of the core component from between the superior and inferior components.

2. The intervertebral fusion device according to claim 1, wherein the first and second fingers are unitary with the inferior component and the intervertebral fusion device further comprises third and fourth fingers and third and fourth recesses, the third and fourth fingers unitary with the superior component and the third and fourth recesses defined by the core component, the third and fourth fingers flexing apart in the transverse direction at the end of the first stage of insertion of the core component, a third protrusion defined by the third finger received in the third recess and a fourth protrusion defined by the fourth finger received in the fourth recess during the second stage of insertion of the core component whereby the intervertebral fusion device is configured to provide for resistance to movement of the core component relative to the inferior and superior components.

3. The intervertebral fusion device according to claim 1, wherein each of the first and second protrusions is at a location on the inferior or superior component and each of the first and second recesses is at a location on the core component whereby the first and second protrusions are received in the first and second recesses respectively when the core component is substantially fully inserted between the inferior and superior components.

4. The intervertebral fusion device according to claim 1, wherein the core component has an upper side and a lower side, the upper side facing the superior component bottom side and the lower side facing the inferior component top side when the core component is inserted between the inferior and superior components, wherein the first lateral side extends between the upper and lower sides of the core component, the second lateral side extends between the upper and lower sides of the core component, a part of the first lateral side of the core component is substantially coterminous with the first lateral side of the superior component and the first lateral side of the inferior component, and a part of the second lateral side of the core component is substantially coterminous with the second lateral side of the superior component and the second lateral side of the inferior component.

5. The intervertebral fusion device according to claim 1, wherein the core component comprises at least one core anterior formation at an anterior end of the core component and the inferior or superior component comprises at least one component anterior formation at an anterior end of the inferior or superior component, the at least one core anterior formation and the at least one component anterior formation configured to start inter-engaging near full insertion of the core component between the inferior and superior components and to draw the superior or inferior component and the core component together in the direction of separation of the inferior and superior components upon further insertion of the core component between the inferior and superior components.

6. The intervertebral fusion device according to claim 5, wherein the core component has an upper side and a lower side, the upper side facing the superior component bottom side and the lower side facing the inferior component top side when the core component is inserted between the inferior and superior components, each at least one core anterior formation is an anterior protrusion which protrudes from one of the upper side and the lower side, each at least one component anterior formation is an anterior recess in the anterior end of the respective one of the superior and inferior components, the anterior protrusion and the anterior recess defining surface profiles that cooperate upon reception of the anterior protrusion in the anterior recess to draw the superior or inferior component and the core component together in the direction of separation of the inferior and superior components as an extent of insertion of the core component between the superior and inferior components increases.

7. The intervertebral fusion device according to claim 6, wherein at least one of the surface profile of the anterior protrusion and the surface profile of the anterior recess is sloped with a direction of the slope such that the superior or inferior component and the core component are drawn together in the direction of separation of the inferior and superior components.

8. The intervertebral fusion device according to claim 7, wherein the slope defined by at least one of the anterior protrusion and the anterior recess is inclined to the direction of separation of the superior and inferior components and to an anterior to posterior direction of the intervertebral fusion device.

9. The intervertebral fusion device according to claim 7, wherein the slope defined by the anterior protrusion is formed by a side of the anterior protrusion, the side of the anterior protrusion facing towards the posterior end of the core component, and the side of the anterior protrusion sloping away from a distal end of the anterior protrusion towards an anterior end of the core component.

10. The intervertebral fusion device according to claim 1, wherein the core component comprises a core posterior formation at the posterior end of the core component and the inferior component or superior component comprises a component posterior formation at the posterior end of the inferior or superior component, the core posterior formation and the component posterior formation configured to start inter-engaging near full insertion of the core component between the inferior and superior components and to draw the superior or inferior component and the core component together in the direction of separation of the inferior and superior components upon further insertion of the core component between the inferior and superior components.

11. The intervertebral fusion device according to claim 10, wherein the core posterior formation is a posterior protrusion which protrudes from the posterior end of the core component, the component posterior formation is a component posterior protrusion which protrudes from the posterior end of the superior or inferior component and over the superior component bottom side or over the inferior component top side, the posterior protrusion and the component posterior formation defining surface profiles that cooperate to draw the superior or inferior component and the core component together in the direction of separation of the inferior and superior components as an extent of insertion of the core component between the superior and inferior components increases.

12. The intervertebral fusion device according to claim 11, wherein at least one of the surface profile of the posterior protrusion and the surface profile of the component posterior formation is sloped with a direction of the slope such that the superior or inferior component and the core component are drawn together in the direction of separation of the inferior and superior components.

13. The intervertebral fusion device according to claim 12, wherein the slope defined by at least one of the posterior protrusion and the component posterior formation is inclined to the direction of separation of the superior and inferior components and to an anterior to posterior direction of the intervertebral fusion device.

14. A method of installing the intervertebral fusion device of claim 1 in an intervertebral space between first and second adjacent vertebrae, the method comprising:
    positioning the superior component and the inferior component relative to each other such that the superior component bottom side and the inferior component top side oppose each other;
    inserting the core component between the superior and inferior components whereby a separation between the superior and inferior components is determined; and
    disposing the intervertebral fusion device in the intervertebral space such that the superior component top side abuts against the first vertebra and the inferior component bottom side abuts against the second vertebra,
    wherein inserting the core component between the superior and inferior components comprises receiving the first and second lateral sides of the core component between the first and second fingers during the first stage of insertion of the core component to thereby guide the core component, wherein the posterior end of the core component bears against the first and second protrusions at the end of the first stage of insertion to flex the first and second fingers apart in the transverse direction, and wherein during the second stage of insertion following the first stage of insertion the first and second protrusions are received in the first and second recesses respectively under spring bias exerted by the first and second fingers to thereby present resistance to ejection of the core component from between the superior and inferior components.

15. The intervertebral fusion device according to claim 1, wherein each of the first and second protrusions is at a first distance from the anterior end of the inferior or superior component, and each of the first and second recesses is at a second distance from an anterior end of the core component, the first distance greater than the second distance.

16. The intervertebral fusion device according to claim 1, wherein the superior component defines at least one superior screw aperture near the anterior end of the superior component and the inferior component defines at least one inferior screw aperture near the anterior end of the inferior component, each at least one superior screw aperture at a different location in the transverse direction from each least one inferior screw aperture when the superior and inferior components are in registration, and each at least one superior screw aperture and each at least one inferior screw aperture is configured to receive a bone screw therethrough.

17. The intervertebral fusion device according to claim 16, wherein each at least one superior screw aperture is substantially circular and extends through the superior component from the superior component top side to the superior component bottom side, and each at least one inferior screw aperture is substantially circular and extends through the inferior component from the inferior component top side to the inferior component bottom side.

18. The intervertebral fusion device according to claim 16, wherein the superior component defines solely one superior screw aperture which is near the anterior end of the superior component, the one superior screw aperture located substantially midway across the superior component in the transverse direction, and wherein the inferior component defines solely two inferior screw apertures which are spaced apart in the transverse direction, the two inferior screw apertures located substantially a same distance from midway on the inferior component in the transverse direction.

19. The intervertebral fusion device according to claim 1, wherein the core component has an upper side and a lower side, the upper side facing the superior component bottom side and the lower side facing the inferior component top side when the core component is inserted between the inferior and superior components, the core component defines at least one upper screw aperture near an anterior end and in the upper side of the core component and at least one lower screw aperture near the anterior end and in the lower side of the core component, and each at least one upper screw aperture and each at least one lower screw aperture is configured to receive a bone screw therethrough.

20. The intervertebral fusion device according to claim 19, wherein the superior component defines at least one superior screw aperture near the anterior end of the superior component and the inferior component defines at least one inferior screw aperture near the anterior end of the inferior component, each at least one upper screw aperture substantially in registration with a respective one of each at least one superior screw aperture when the superior component and core component are in registration, and each at least one lower screw aperture substantially in registration with a respective one of each at least one inferior screw aperture when the inferior component and core component are in registration.

21. The intervertebral fusion device according to claim 19, wherein each at least one upper screw aperture is a recess which extends from an anterior end of the core component towards the posterior end of the core component, and each at least one lower screw aperture is a recess which extends from an anterior end of the core component towards the posterior end of the core component.

* * * * *